(12) United States Patent
Smith et al.

(10) Patent No.: US 7,783,346 B2
(45) Date of Patent: Aug. 24, 2010

(54) ILLUMINATED INFUSION CANNULA

(75) Inventors: Ronald T. Smith, Newprt Coast, CA (US); Jack R. Auld, Laguna Niguel, CA (US); Christopher McCollam, Irvine, CA (US); Dean Y. Lin, Chino Hills, CA (US); Dyson Hickingbotham, Stouchsburg, PA (US)

(73) Assignee: Alcon, Inc., Hunenberg (CH)

( * ) Notice: Subject to any disclaimer, the term of this patent is extended or adjusted under 35 U.S.C. 154(b) by 599 days.

(21) Appl. No.: 11/612,234

(22) Filed: Dec. 18, 2006

(65) Prior Publication Data

US 2007/0179430 A1 Aug. 2, 2007

Related U.S. Application Data

(60) Provisional application No. 60/751,175, filed on Dec. 16, 2005.

(51) Int. Cl.
*A61N 1/30* (2006.01)
*A61B 18/18* (2006.01)

(52) U.S. Cl. .............. 604/21; 604/20; 604/117; 606/4; 600/249

(58) Field of Classification Search .......... 604/4, 604/21; 606/16; 600/156–183, 162, 178
See application file for complete search history.

(56) References Cited

U.S. PATENT DOCUMENTS

| 4,551,129 A | | 11/1985 | Coleman et al. |
| 4,699,140 A | * | 10/1987 | Holmes et al. .............. 606/107 |
| 4,820,264 A | * | 4/1989 | Matsui et al. ................. 604/21 |
| 5,643,250 A | * | 7/1997 | O'Donnell, Jr. ................ 606/4 |
| 5,725,514 A | * | 3/1998 | Grinblat et al. ............. 604/294 |
| 6,419,627 B1 | * | 7/2002 | Ben Nun .................... 600/125 |
| 6,936,053 B1 | | 8/2005 | Weiss |
| 2003/0169603 A1 | * | 9/2003 | Luloh et al. ................. 362/574 |
| 2006/0184162 A1 | | 8/2006 | Smith |

FOREIGN PATENT DOCUMENTS

WO WO2005086693 9/2005

* cited by examiner

*Primary Examiner*—Nicholas D Lucchesi
*Assistant Examiner*—Leah Stohr
(74) *Attorney, Agent, or Firm*—Jonathan E. Prejean

(57) ABSTRACT

A transparent illuminated infusion cannula is provided for illuminating an area during eye surgery. An optical fiber may be spaced a certain distance away from the cannula such that fluid flow around the distal end of the fiber and into the transparent cannula may occur with a much higher flow rate than what had previously been possible. The fiber cannula airspace may be optimized so that the cross-sectional area of the fluid conduit remains substantially constant in order to achieve a best compromise between high light transmittance and high fluid flow rate.

24 Claims, 21 Drawing Sheets

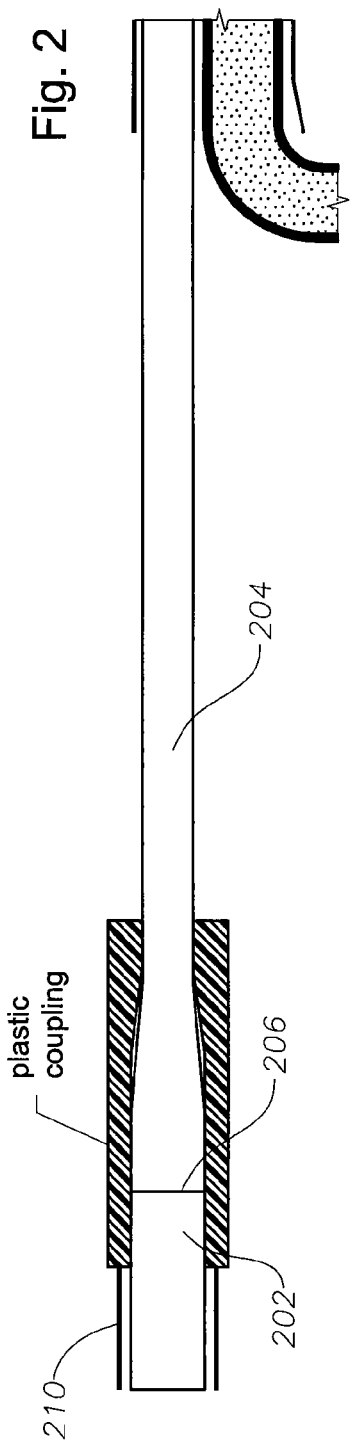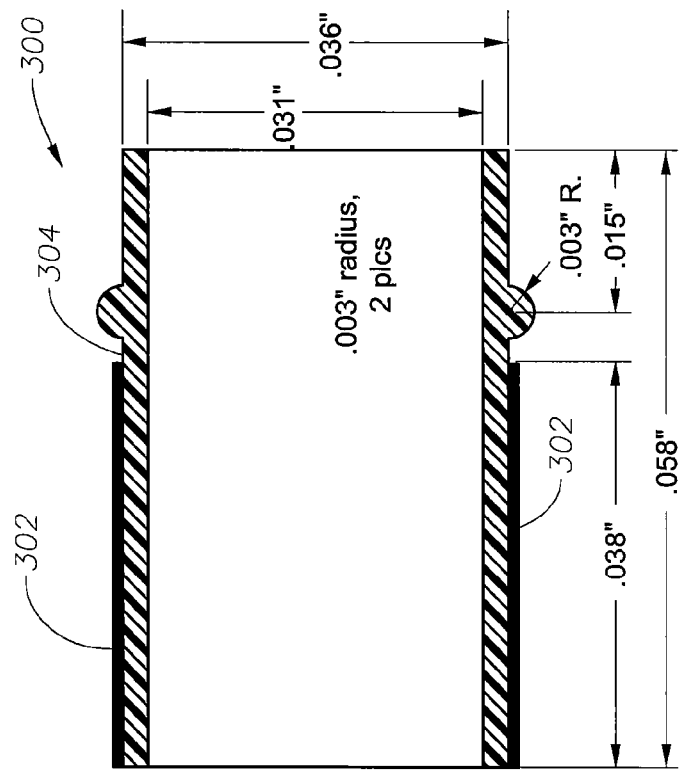

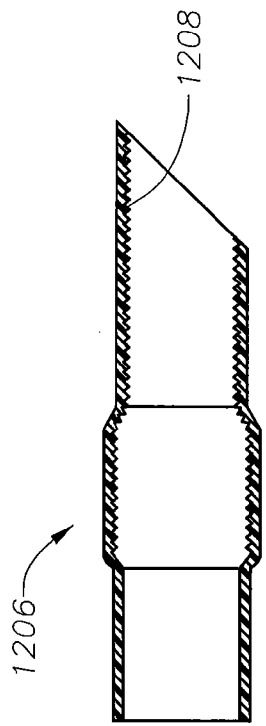
Fig. 12
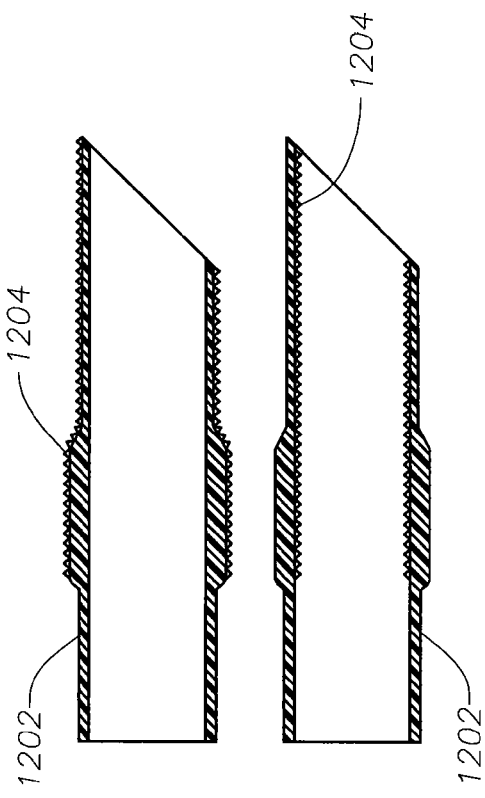
Fig. 13

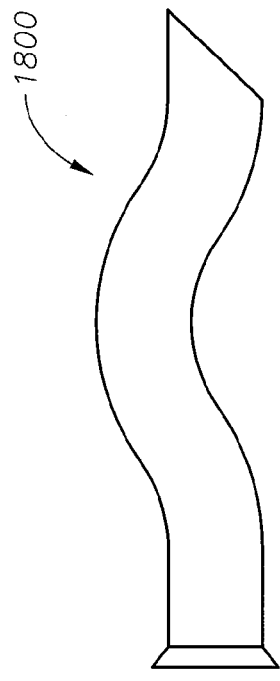
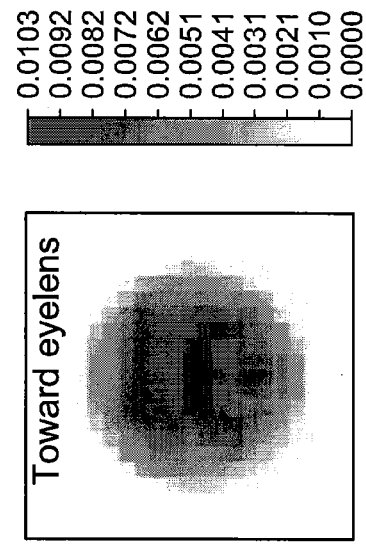
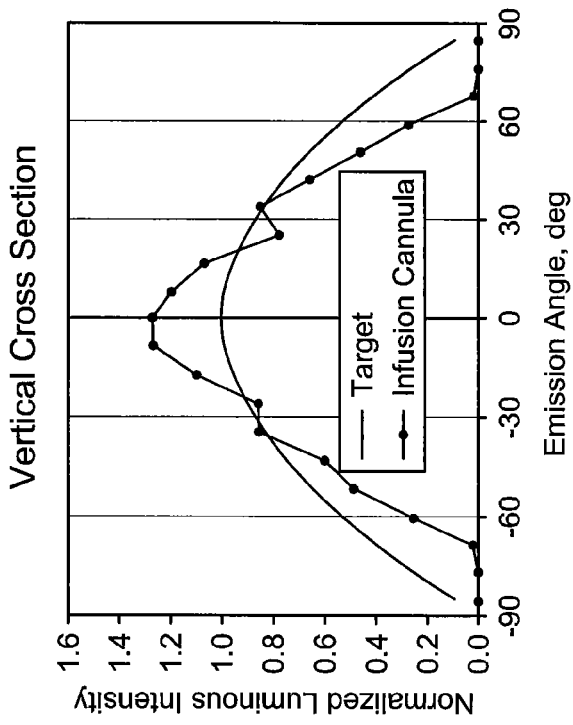
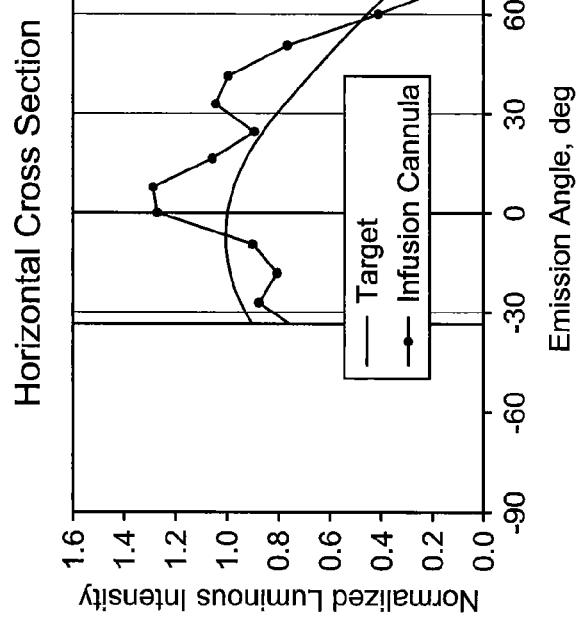
Fig. 18

Fig. 22
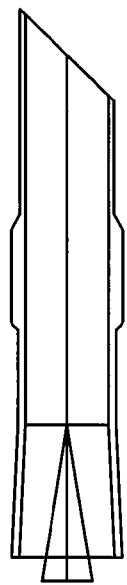
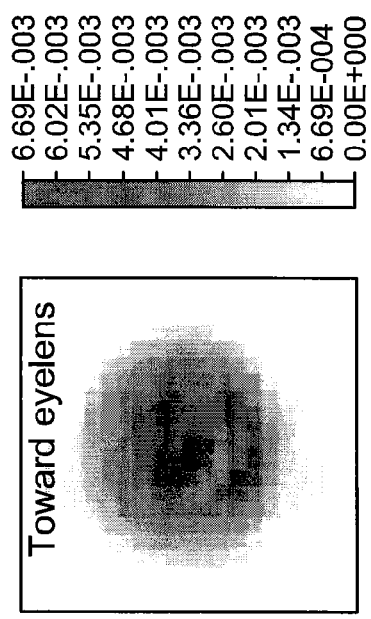
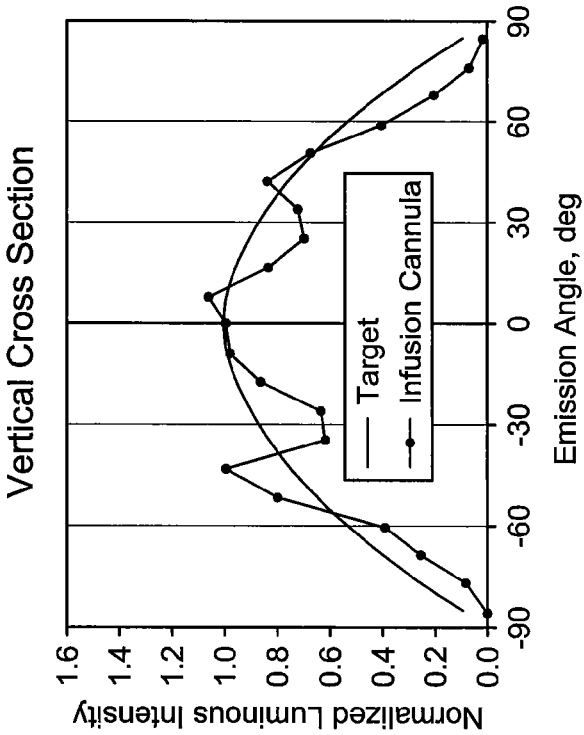
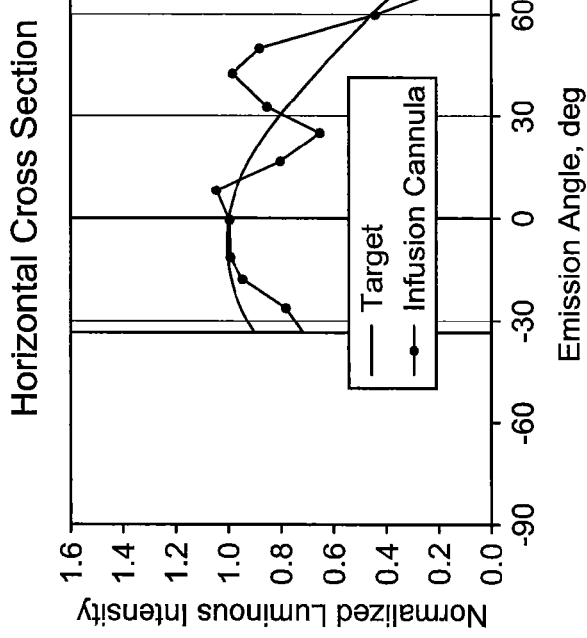

ILLUMINATED INFUSION CANNULA

RELATED APPLICATIONS

This application claims the benefit of, priority to, and incorporates by reference in its entirety for all purposes U.S. Provisional Application No. 60/751,175 entitled "Transparent Illuminated Infusion Cannula" filed on Dec. 16, 2005.

This application is related to and incorporates by reference in its entirety for all purposes U.S. Provisional Application No. 60/653,265 filed on Feb. 15, 2005, entitled "High Throughput Endo-Illuminator Probe."

This application is related to and incorporates by reference in its entirety for all purposes U.S. Non-Provisional application Ser. No. 11/354,615 filed on Feb. 15, 2006, entitled "High Throughput Endo-Illuminator Probe."

TECHNICAL FIELD OF THE INVENTION

The present invention relates generally to surgical instrumentation. In particular, the present invention relates to surgical instruments for illuminating an area during eye surgery. Even more particularly, the present invention relates to an infusion instrument having an illumination unit for illuminating the inside of an eyeball.

BACKGROUND OF THE INVENTION

In ophthalmic surgery, and in particular in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle illuminators can thus illuminate a larger portion of the retina as required by current wide-angle surgical microscope systems.

It is also known to incorporate optical fibers into the working end of a surgical instrument. This eliminates the need for a separate illumination port and offers the advantage of directing the light beam together with the instrument onto the target site. Instrument sizes must, however, be correspondingly increased and larger sclerotomies may be necessary. An alternative procedure is to employ an illuminated infusion cannula to integrate the infusion and illumination functions at a single point.

One example of a combined infusion cannula and illumination source is given in U.S. Pat. No. 4,820,264. The '264 device comprises an infusion channel through which light transmitting fibers are passed for directing light into the eyeball at the point of discharge of the intraocular irrigating solution. Such illumination is not automatically directed by manipulation of the cutting instruments. Moreover, the fibers are run directly within the infusion channel, and illumination and infusion portions are non-separable near the eye.

These prior art combined infusion cannulas, however, exhibit various disadvantages. These disadvantages include undesirably low light transmittance and undesirable fluid flow rates, particularly when combined in, for example, a 20 gauge cannula.

Therefore, a need exists for an illuminated infusion cannula that can reduce or eliminate the problems prior art combined cannulas, particularly low light transmittance and low fluid flow rates.

SUMMARY OF THE INVENTION

Embodiments of the present invention provide a system and method for illuminating an area during eye surgery that substantially addresses the above identified needs as well as other needs. One embodiment provides a transparent illuminated infusion cannula operable to illuminate an area during eye surgery. An optical fiber may be spaced a certain distance away from the cannula such that fluid flow around the distal end of the fiber and into the transparent cannula may occur with a much higher flow rate than what had previously been possible. The fiber cannula airspace may be optimized so that the cross-sectional area of the fluid conduit remains substantially constant in order to achieve a best compromise between high light transmittance and high fluid flow rate.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein:

FIG. 2 provides a representation of a transparent illuminated infusion cannula's upstream end in accordance with embodiments of the present invention;

FIG. 3 provides a representation of a transparent illuminated infusion cannula in accordance with embodiments of the present invention;

FIGS. 12-14 depict various optical features of the transparent illuminated infusion cannula in accordance with embodiments of the present invention;

FIG. 18 depicts a solution to the "hot spot" problem illustrated in FIG. 15 that employs a curved transparent cannula design that results in an angularly broad output beam in either gas (such as air) or liquid (such as saline solution) in accordance with embodiments of the present invention;

FIG. 22 depicts the resultantly large angular spread of the emitted beam in air associated with the transparent illuminated infusion cannula of FIGS. 19-21 in accordance with embodiments of the present invention;

DESCRIPTION OF THE INVENTION

Preferred embodiments of the present invention are illustrated in the FIGs., like numerals being used to refer to like and corresponding parts of the various drawings.

Figure 1:
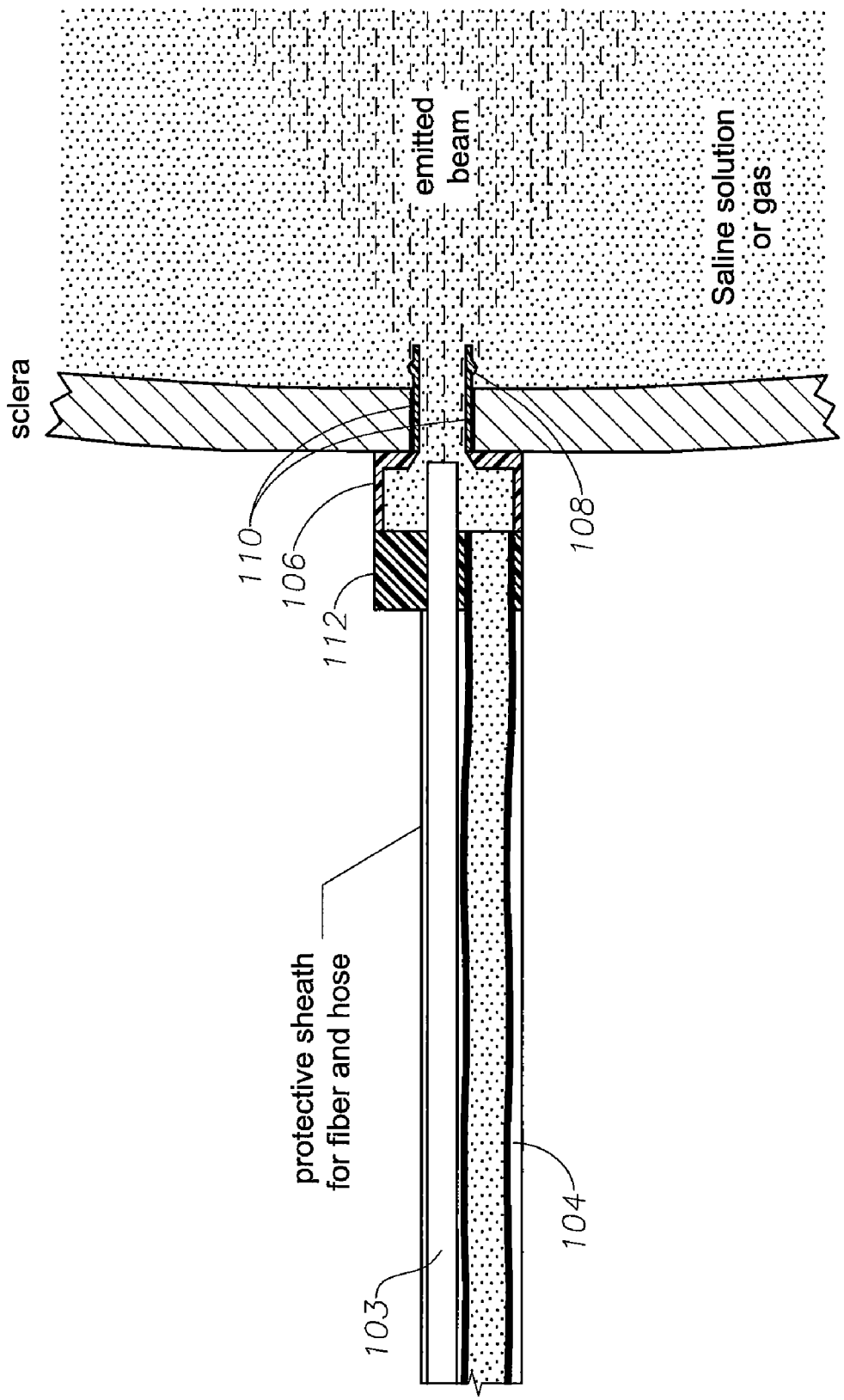
FIG. 1 provides a representation of a transparent illuminated infusion cannula's downstream end in accordance with embodiments of the present invention.

FIG. 1 provides a representation of a transparent illuminated infusion cannula's downstream end in accordance with embodiments of the present invention. This embodiment provides an illuminated infusion cannula 100 that may include the following components: (1) an endo-illuminator 100 incorporating a tapered high numerical aperture (NA) optical fiber 101, such as a belled 20 mil diameter 0.63 NA Toray fiber 103, (2) a hose 104 for the transport of liquid or gas, (3) a hub 106 where the endo-illuminator and hose come together, (4) a transparent cannula 108 downstream from the hub which may incorporate a self-retaining ring, and (5) and a highly reflective coating 110 on a portion of the outer side surface of the cannula. Optionally the distal portion of the transparent cannula may be curved or may incorporate features such as a diffusive, diffractive or microns array surface to disperse the light into a desired angular distribution.

FIG. 2 provides a representation of a transparent illuminated infusion cannula's upstream end in accordance with embodiments of the present invention. This upstream end may incorporate a "High-throughput illuminator probe" disclosed in commonly owned U.S. Provisional Patent Application No. 60/653,265 and filed on Feb. 15, 2005, and U.S. Non-Provisional patent application Ser. No. 11/354,615 and filed on Feb. 15, 2006, which are hereby incorporated by reference in their entirety for all purposes.

The steps to create an infusion cannula's upstream end in accordance with embodiments of the present invention may involve several steps. First, a medium-NA, large diameter fiber 202 may be joined to a high NA tapered fiber 204 as described in U.S. Provisional Patent Application No. 60/653, 265, and filed on Feb. 15, 2005. As an example, join a 29.5 mil diameter, 0.5 NA fiber 202 to a 29.5→20 mil tapered, 0.63 NA Toray fiber 204 using Dymax 142-M optical adhesive 206. Next a flexible plastic hose 208 may be provided for transporting fluid or gas. Optionally, the fiber 202 and hose 208 can be enclosed within a protective sheath 210 to create a single cable. Next a glass cylindrical cannula, which is long enough to pass through the sclera (at least 0.53") and which optionally has a toroidal retaining ring to enable to cannula to remain within the eye once inserted, is machined or injection molded from transparent plastic.

FIG. 3 provides a representation of a transparent illuminated infusion cannula in accordance with embodiments of the present invention. In this example, a 20 gauge transparent cannula 300 may be made of acrylic and can have an inner diameter of 31 mils, an outer diameter of 36 mils, and a length of 58 mils. Coatings 302 may be applied to a portion of the inner or outer diameter cylindrical surface 304 of the cannula 300 with a metallic or dielectric multilayer coating process or other like process. In the example of FIG. 3, a 38 mil length of the outer cylindrical surface of the cannula is coated. The coating should have high reflectance and be biocompatible. Silver and aluminum are coatings which are highly reflective to visible light and which should have acceptable biocompatibility.

Returning to FIG. 1, plastic hub 106 and plastic cap 112, formed by machining or injection molding, join the fiber 103 and fluid hose 104 to the transparent cannula 108. The plastic hub 106 and plastic cap 112 can be made separately then snapped and/or glued together, or the plastic hub 106 and cap 112 could be made as one single part. The transparent cannula 108 is snapped and/or glued into the distal end of the plastic hub 106. Alternatively, the transparent cannula and hub could be made as one contiguous part. The plastic cap has two holes—one for the fiber and one for the plastic fiber. The fiber and hose are inserted into the cap. The plastic cap positions the fiber laterally so that it is coaxial with the transparent cannula axis. The fiber 103 is inserted through the plastic cap 112 so that its distal end is spaced the correct distance from the proximal end of the cannula (see the "fundamental principles" discussion below) then the fiber is bonded to the plastic cap 112.

Figure 4:
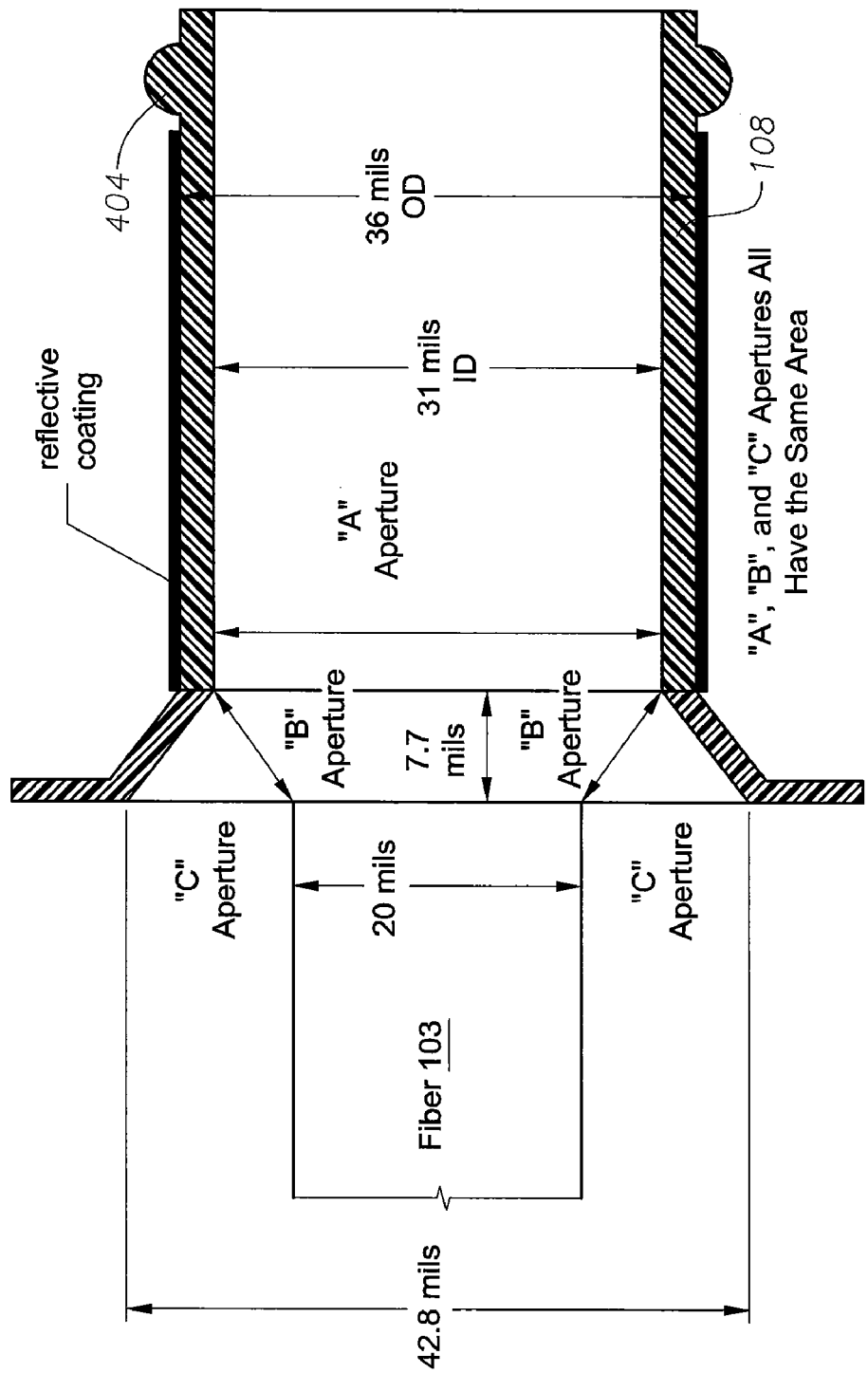
FIG. 4 provides a representation of fiber/20 gauge cannula example configuration in accordance with embodiments of the present invention.

FIG. 4 provides a representation of fiber 103 (20 gauge) cannula 108 configuration in accordance with embodiments of the present invention. In this example, the fiber-cannula spacing is 7.7 mils. In addition, the plastic hose 104 can be glued to the plastic cap 112 if necessary.

The transparent illuminated infusion cannula provided by embodiments of the present invention provides: (1) higher light transmittance than competing illuminated infusion cannula; (2) better fluid flow rate than competing illuminated infusion cannula; (3) simultaneously incorporates improved light transmittance and improved flow rate in the same illuminated infusion cannula; and (4) achieves the high light transmittance and high flow rate through a 20 gauge cannula.

The principles described in U.S. Provisional Patent Application No. 60/653,265 allow light to pass through a small aperture (the aperture at the distal end of the tapered high-NA fiber) while achieving very high relative light transmittance. The aperture at the distal end of the fiber is smaller than the transparent cannula aperture.

Since the tapered fiber distal aperture is smaller than the transparent cannula aperture, nearly all of the light emitted by the fiber will pass through the inner-diameter aperture at the proximal end of the transparent cannula even if the distal end of the fiber is spaced a certain distance away from the proximal end of the transparent cannula. The maximum separation distance for maintaining high throughput is roughly defined as $S=[(D_c-D_f)/2]/\tan \theta_{cutoff}$, where $D_c$=the transparent cannula inner diameter, $D_f$=the diameter at the fiber distal end, and $\theta_{cutoff}$=the cutoff angle of the fiber. For a 0.63 NA, 20 mil Toray fiber in air and a 31 mil transparent cannula inner diameter, then the cutoff angle=39.1° and the maximum separation distance S=6.8 mils.

If the transparent cannula is not coated, the rays of light entering the inner-diameter proximal aperture of the cannula will pass through the walls of the cannula and be lost by absorbance within the sclera. However, if a portion of the inner or outer diameter cylindrical side wall of the cannula (the portion that passes through the sclera) is coated with a high reflectance metallic or multilayer dielectric coating, the light within the cannula will be reflected by the coating so that it remains within the cannula as it passes through the sclera. The coating is designed to end once the cannula emerges from the sclera. When the light passes through the portion of cannula that is not coated, it will pass through the cannula wall and will illuminate the retina within the interior of the eye.

Spacing the fiber and cannula a certain distance away from each other, allows fluid to flow around the distal end of the fiber and into the transparent cannula with a much higher flow rate than would have been possible if the fiber-cannula separation S was 0. Embodiments of the present invention provide a fiber/cannula interface so that the cross-sectional surface area of the fluid conduit is optimized everywhere (i.e. no locations exist where the cross-sectional area of flow is small). Flow rate should be roughly proportional to cross-sectional area.

The fiber/cannula interface is designed to achieve a best compromise between high light transmittance and high fluid flow rate. In the 20 gauge configuration described in FIG. 4, the theoretically predicted light transmittance in air (relative to a 20 gauge, 29.5 mil diameter, and 0.5 NA fiber) is ~82% and the flow area is 0.000755 square inches. This represents a 1.71× improvement in light transmittance and 1.74× improvement in flow area over some prior art illuminated infusion cannula designs (see "Prior Art").

An annular self-retaining "bump" 404 on the outer cylindrical surface of the cannula is designed to cause the illuminated infusion cannula to stay put within the eye after insertion.

Embodiments of the present invention maximize light transmittance and flow rate through an illuminated infusion cannula into the eye given, for example, the following constraints:

The illuminator lamp is designed to focus light into a 20 gauge (0.0295" diameter) fiber The infusion cannula must have an outer diameter no larger than 0.036" to permit self-suturing 20 gauge surgery.

The infusion cannula must have a minimum wall thickness to maintain minimum stiffness.

There are many prior attempts to address this problem. Synergetics has a commercially available 20-gauge illuminated infusion cannula probe that consists of (1) a 500 micron (20 mil) diameter, several-foot long, presumably 0.5 NA untapered fiber, (2) a flexible plastic hose for carrying fluid or gas, (3) a hub which joins the optical fiber and plastic hose several inches upstream from the distal end of the fiber (4) a section of fiber and house downstream from the hub in which the fiber is inside the hose, (5) a 20 gauge metal cannula with a 31 mil ID that the hose/fiber combination fit into (the hose slides over the cannula, while the fiber is threaded through the cannula), and (6) a 40 mil long distal end of the fiber past the distal end of the cannula in which the fiber linearly tapers down to a virtual point. This design yields a cross-sectional flow area of 0.000441 square inches and a measured light transmittance (in air) of 47% relative to an Alcon standard 20 gauge endo-illuminator (using the Accurus or AHBI illuminator).

The problem with this design is that the optical fiber and fluid compete for the same cross-sectional area within the fixed 31 mil ID interior of the 20 gauge cannula. Therefore, there is a direct tradeoff between fiber cross-sectional area (and consequentially light transmittance) and fluid cross-sectional area (and consequentially fluid flow rate). When one goes up, the other one goes down proportionally. There is no way in this approach to avoid this tradeoff.

A second solution is provided by Alcon, which provides a 19 gauge illuminated infusion cannula which is similar to the Synergetics design except that: (1) the cannula OD is 42.5 mils, (2) the cannula ID is 37.5 mils, (3) the fiber diameter is 30 mils, and (4) the fluid cross-sectional area is 0.000398 square inches.

Like the Synergetics design, the problem with this design is that the optical fiber and fluid compete for the same cross-sectional area within the fixed 37.5 mil ID interior of the 19 gauge cannula. Therefore, there is a direct tradeoff between fiber cross-sectional area (and consequentially light transmittance) and fluid cross-sectional areas (and consequentially fluid flow rate). When one goes up, the other one goes down proportionally. There is no way in this approach to avoid this tradeoff.

Another problem with this design is the outer diameter is 19 gauge (42.5 mils) instead of 20 gauge (36 mils). The larger cannula size makes the eye surgery more traumatic, prevents self-suturing, and causes healing time to be longer.

The embodiments of the present invention provide various advantages over these prior solutions. For example, a 20 gauge instead of 19 gauge illuminated infusion cannula may be provided. The smaller 20 gauge size (36 mil OD) for the new design leads to less traumatic eye surgery, self-suturing, and reduced healing times.

In the example embodiment of FIG. 4, a 1.74× improvement in light transmittance (in air) is realized when compared to the Synergetics prior art (using the Accurus or AHBI illuminator). Also, a 1.71× improvement in cross-sectional area and flow rate over the Synergetics prior art and a 1.90× improvement in cross-sectional area and flow rate over the Alcon prior art is realized.

Figure 5:
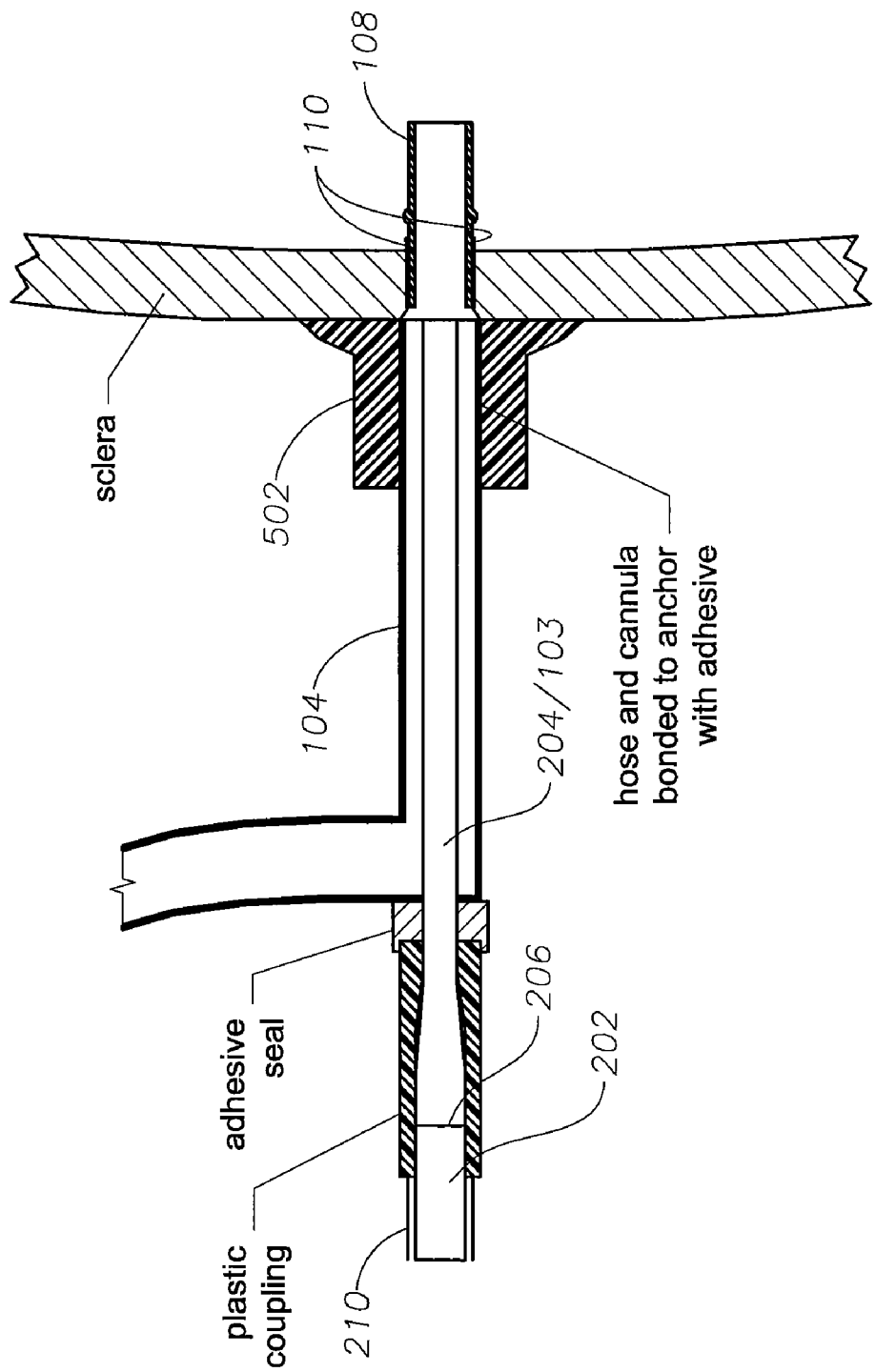
FIG. 5 provides a representation of a transparent illuminated infusion cannula where the fiber and fluid hose come together upstream from the sclera entrance aperture in accordance with embodiments of the present invention.
Figure 6:
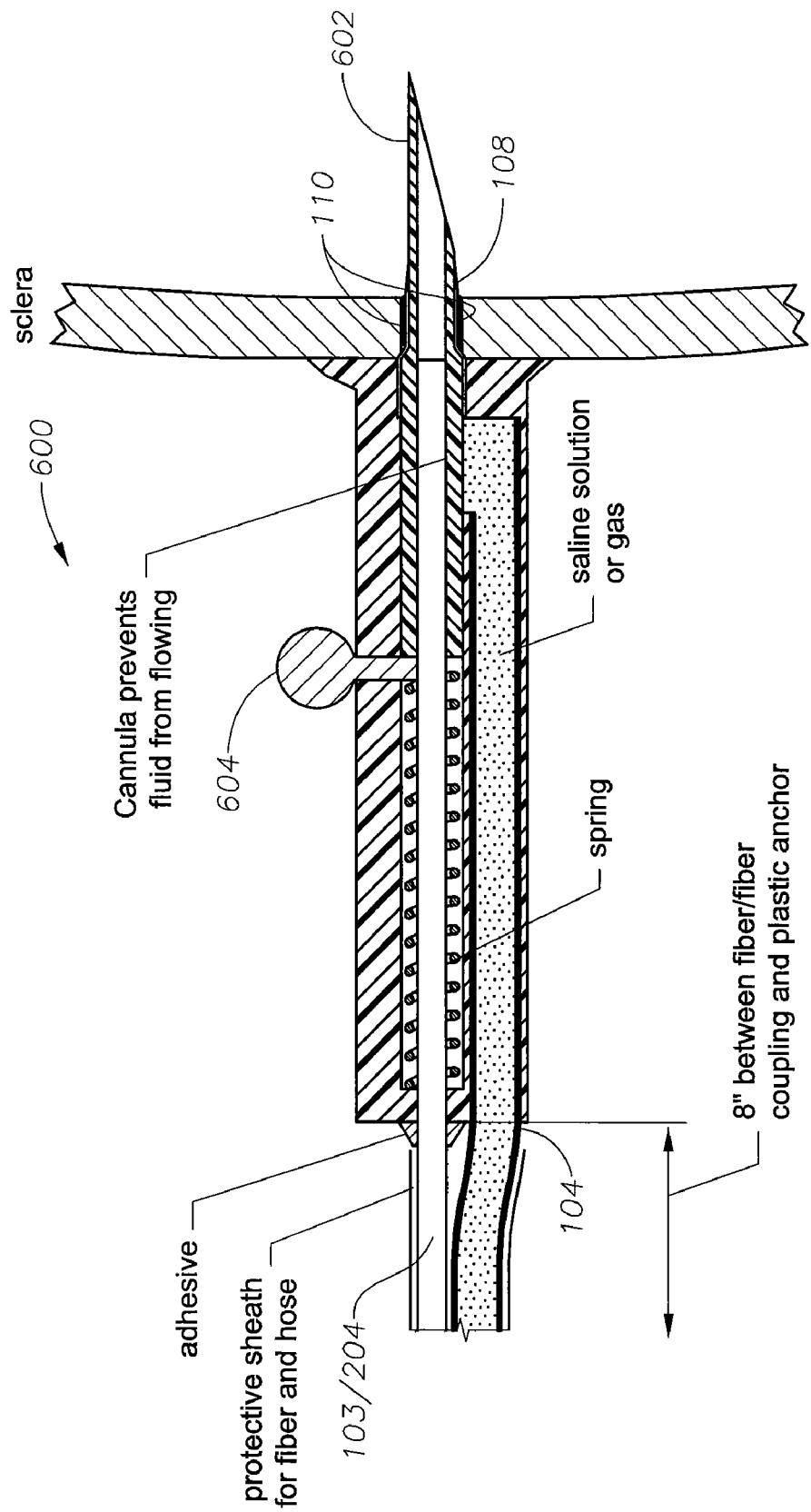
FIG. 6 provides a representation of a self-incisioning (and self-retaining if the annular bump is added to the cannula) transparent illuminated infusion cannula in accordance with embodiments of the present invention.
Figure 7:
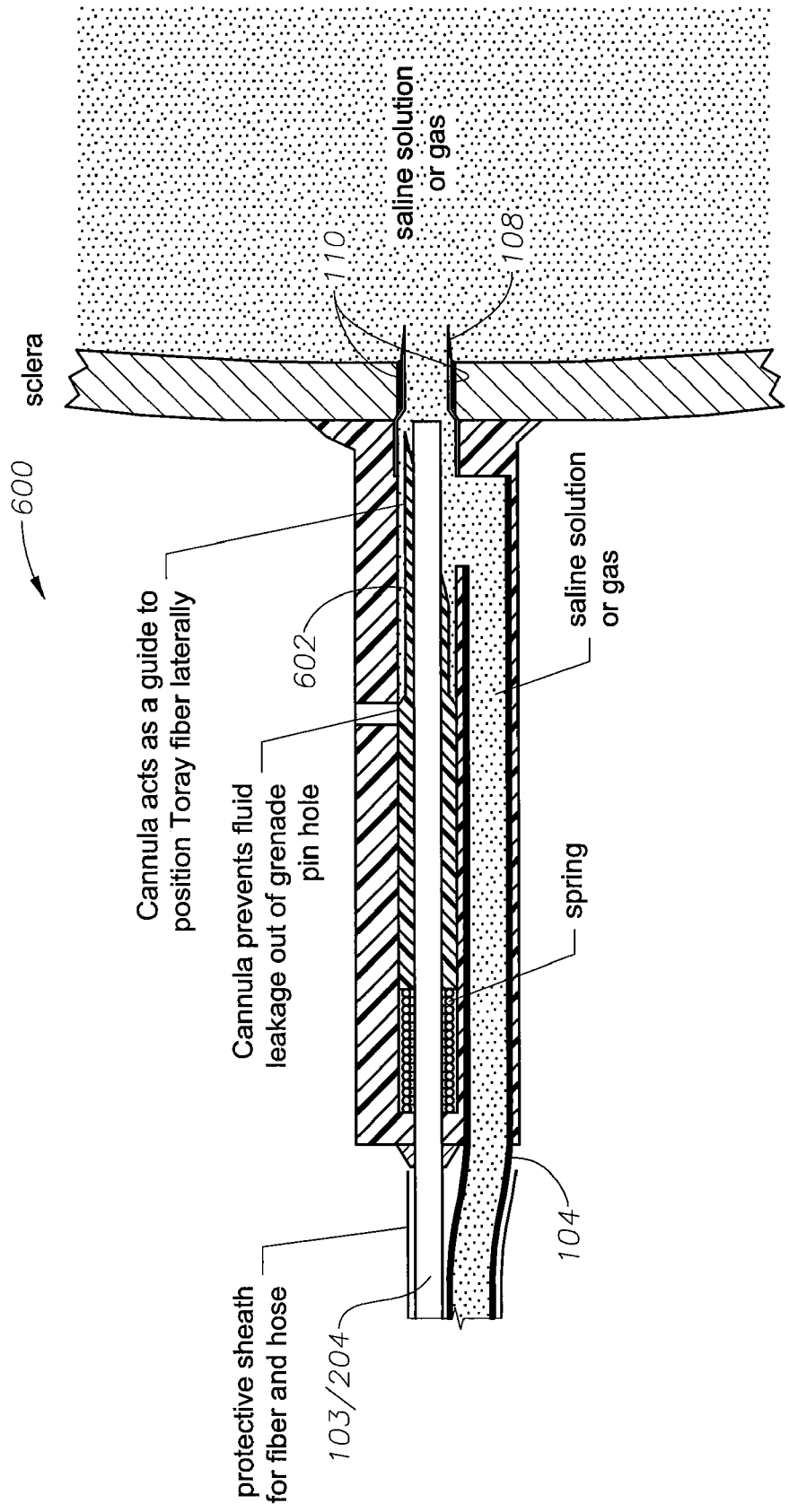
FIG. 7 provides a representation of self-incisioning (and self-retaining if the annular bump is added to the cannula) transparent illuminated infusion cannula in accordance with embodiments of the present invention.
Figure 8:
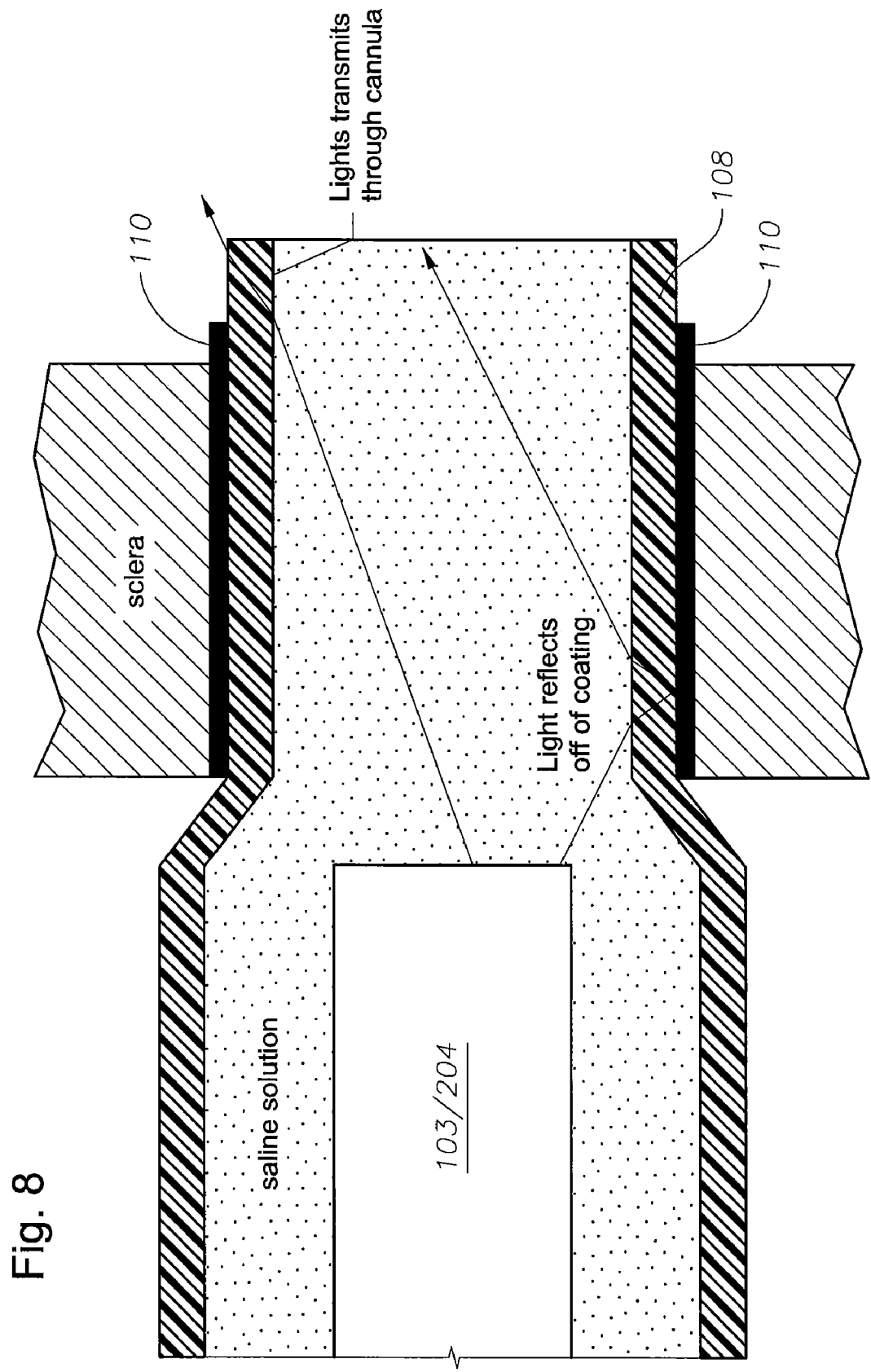
FIGS. 8-11 illustrate the passage of discrete rays and the entire beam through the cannula in both fluid (e.g. saline) mode and gas (e.g. air) mode in accordance with embodiments of the present invention.
Figure 9:
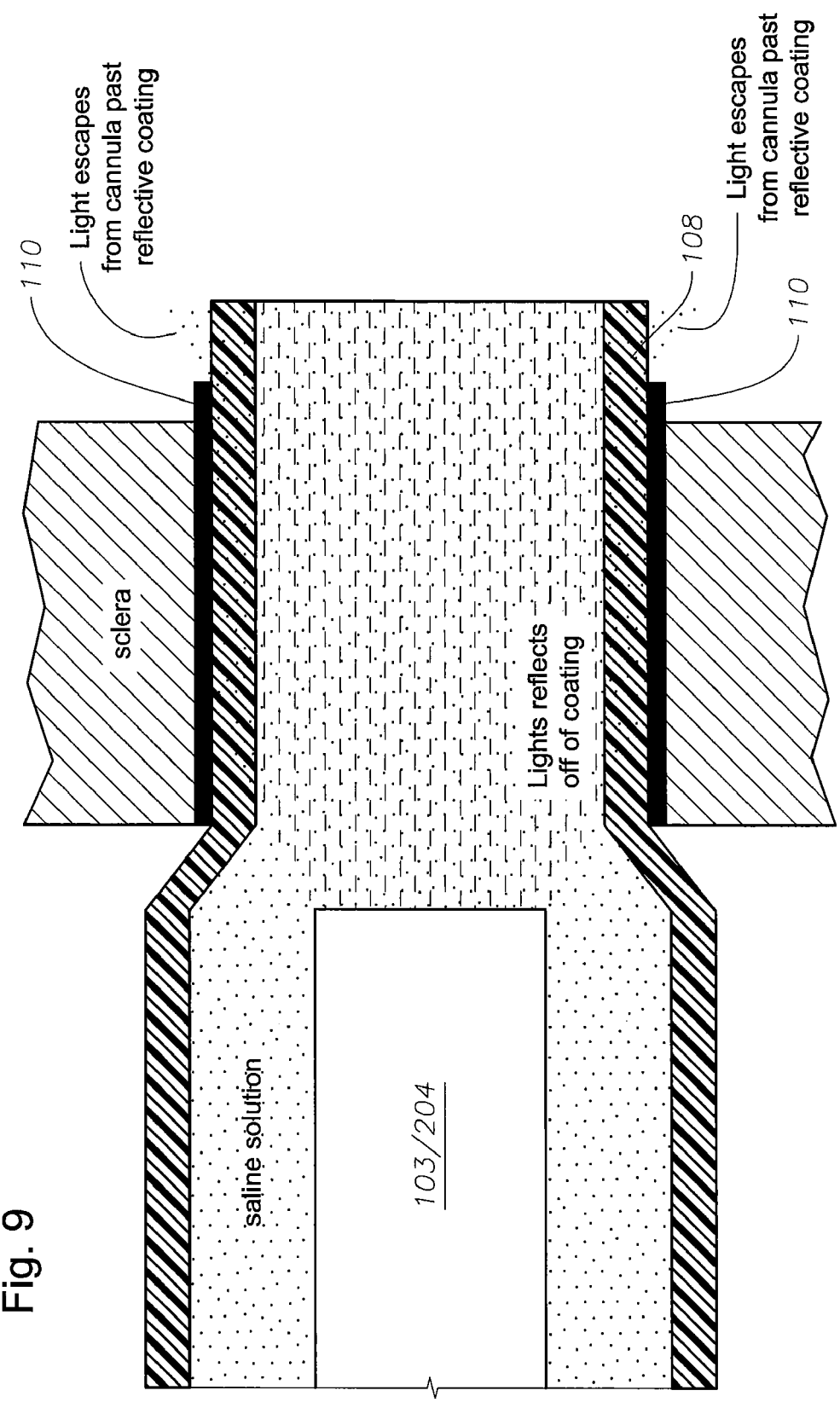
Figure 10:
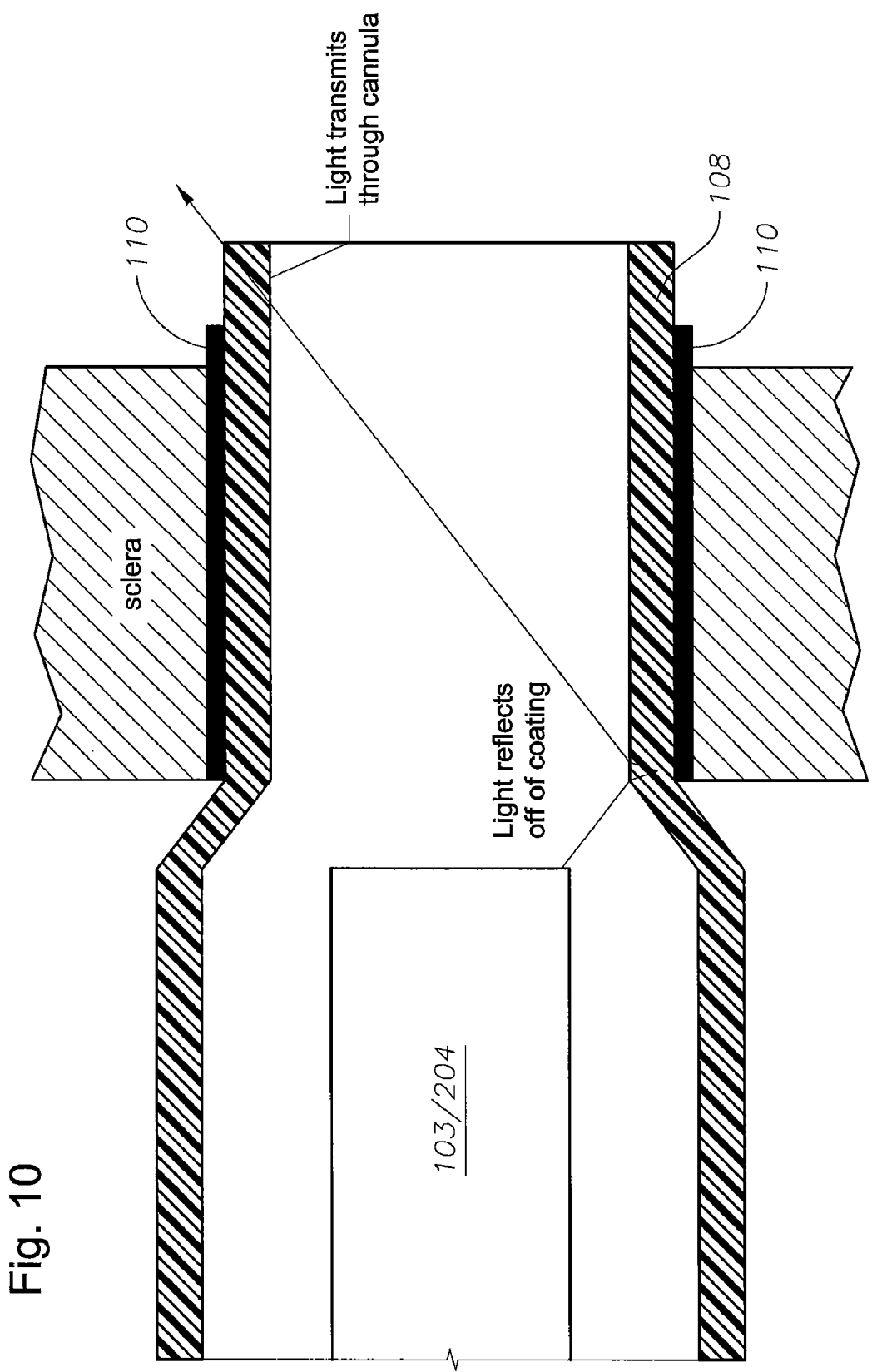
Figure 11:
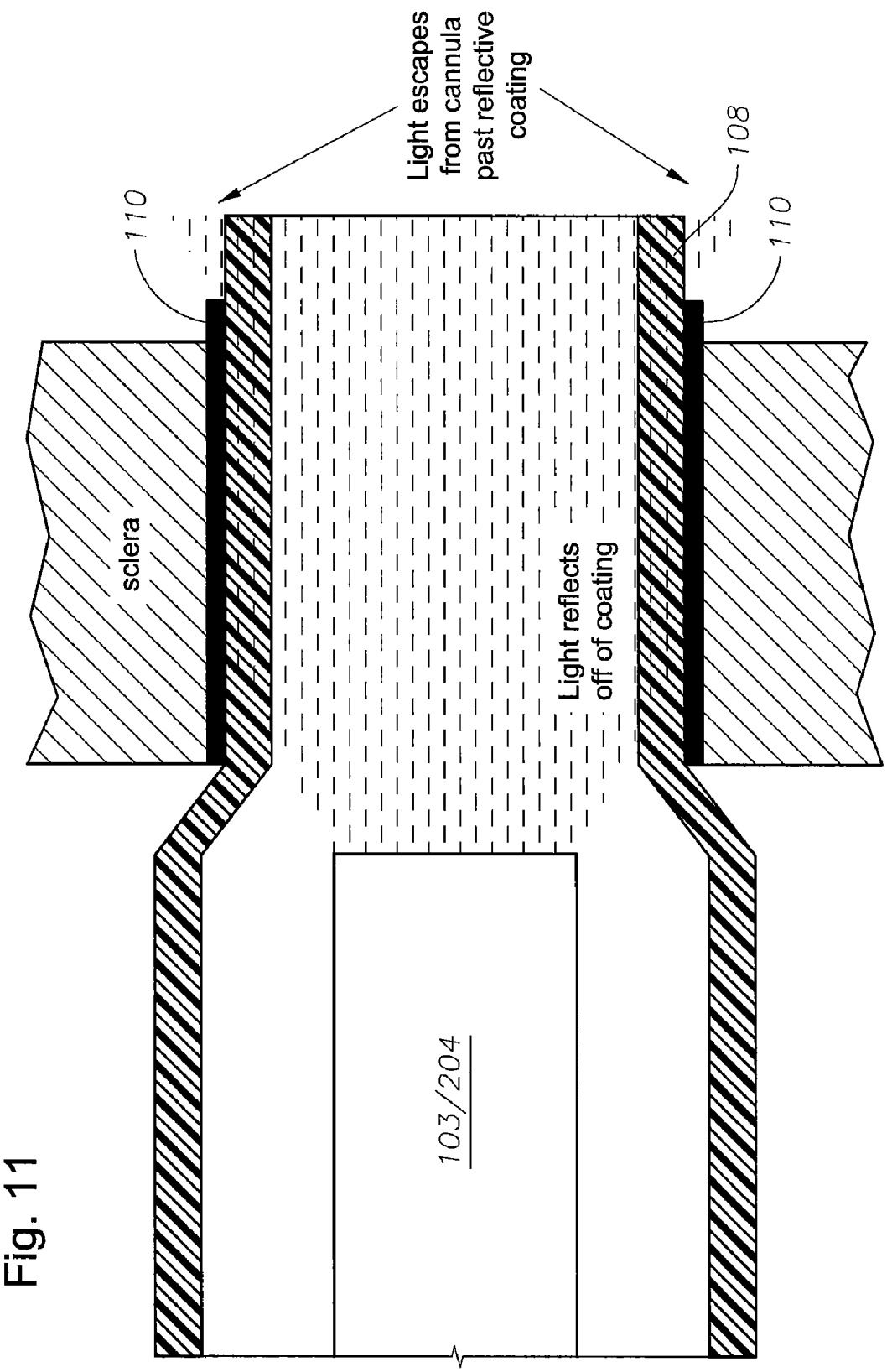

FIGS. 5-7 illustrate other possible embodiments of this invention. FIG. 5 provides a representation of a transparent illuminated infusion cannula where the fiber 103/204 and fluid hose 104 come together upstream from the sclera entrance aperture in accordance with embodiments of the present invention. FIGS. 6 and 7 describe a self-incisioning (and self-retaining if the annular bump is added to the cannula) transparent illuminated infusion cannula 600 that incorporates a spring-loaded metallic incisioning cannula 602 and grenade pin 604. In its initial position, as shown in FIG. 6, the incision cannula 602 is extended to enable an incision in the sclera to be made. When the grenade pin 604 is pulled, the incision cannula 602 retracts, as shown in FIG. 7, leaving the optical fiber 103/204 and transparent cannula 108 in their correct relative positions to provide the optimal combination of light transmittance and fluid flow.

FIGS. 8-11 illustrate the passage of discrete rays and the entire beam through the cannula in both fluid (e.g. saline) mode and gas (e.g. air) mode in accordance with embodiments of the present invention. In gas mode, the angular spread of the beam is wider than in saline mode. Therefore, any light transmittance losses caused by light missing the cannula proximal entrance aperture (due to the fiber/cannula spacing being too large) will be greater in gas mode than in fluid mode.

The prior art discussed above incorporate an optical fiber whose distal end tapers down to a near point. The result of this taper is an angular broadening of the emitted beam into a larger angle than the beam emitted from the untapered fiber. The embodiments of the transparent illuminated infusion cannula described in FIGS. 1-11 incorporate an untapered fiber and a straight, untapered cannula. Therefore, the angular spread of the light emitted from this embodiment is roughly equal to the angular spread from the untapered fiber itself; i.e. much narrower in angular spread than the prior art. For some implementations of this invention, it would be desirable to increase the angular spread of the emitted beam so that the illumination across the retina is relatively uniform. There are two ways of increasing angular spread of the emitted beam: (1) modify the cannula, (2) modify the fiber.

One cannula modification is to make portions or all of the cannula reflective by using metallic or dielectric coatings over selected areas of the transparent cannula, or by making the cannula itself out of reflective metal. Other cannula modifications involve incorporating optical features such as a diffusive surface, a diffractive surface, and/or a micro lens array to disperse the light into a desired angular distribution. Alternatively, a diffusive, diffractive, reflective, or refractive film may be applied like a decal to the outer cylindrical surface of the distal portion of the transparent cannula to provide the desired light distribution. These optical features are described in FIGS. 12-14.

Figure 14:
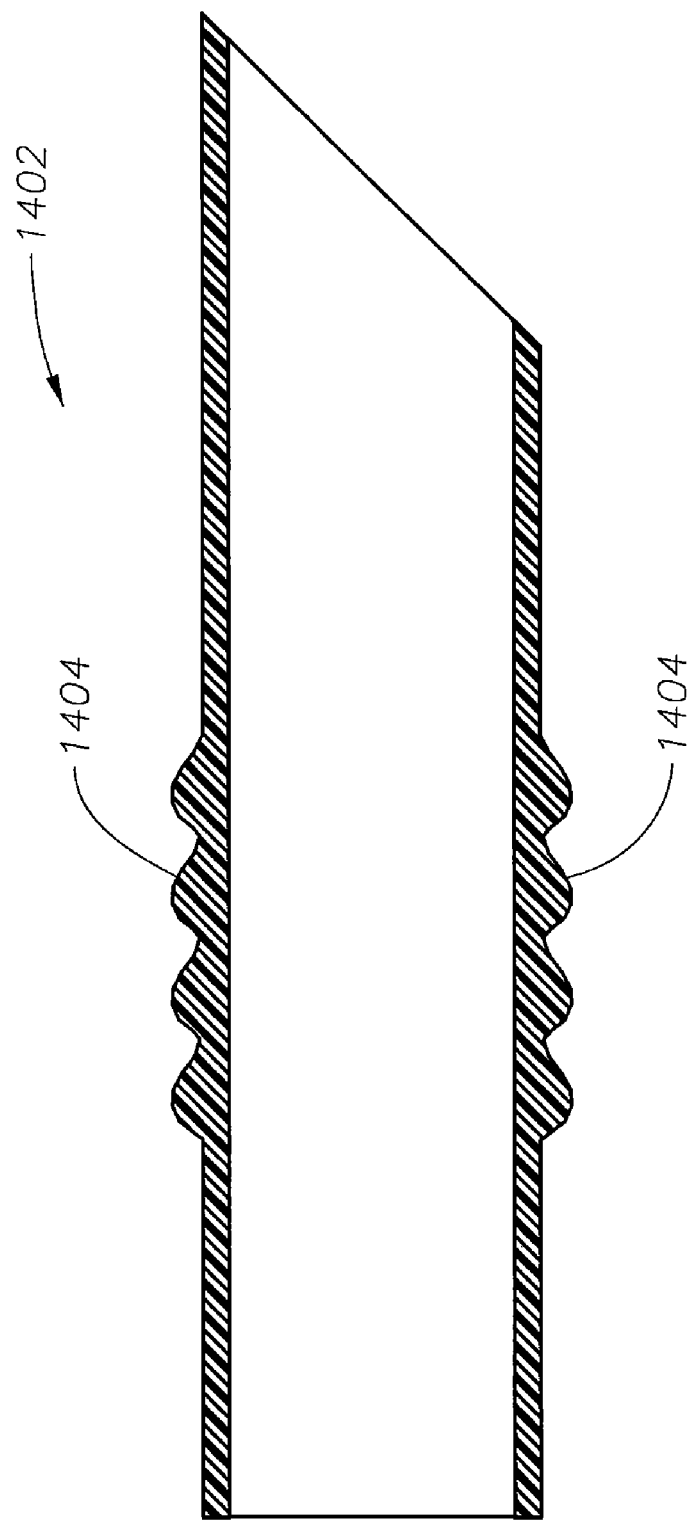

FIG. 12 provides a transparent cannula 1202 having a surface diffuser 1204 located on the outside of the cannula 1202 or the inside of the cannula 1202. Also an opaque cannula 1206 may be provided having a surface diffuser 1208 located on an inner diameter of the cannula. FIG. 13 depicts the use of diffusing paints 1302 on an inner surface or outer surface of cannula 1304 or the use of a bulk plastic diffuser material 1306 for cannula 1304. FIG. 14 provides a transparent cannula 1402 wherein reflective lenses 1404 are applied to the cylindrical surfaces in order to provide a desired light distribution.

Figure 15:
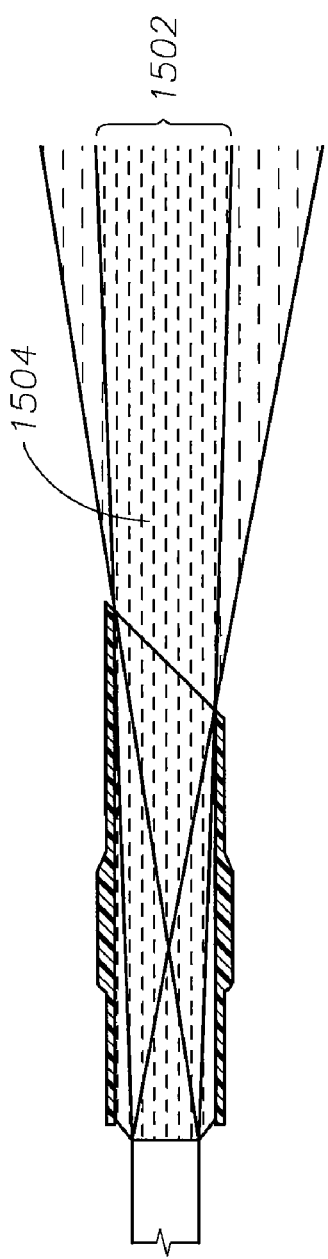
FIG. 15 depicts a "hot spot" created by undiffused light passing directly from the distal end of the fiber through the opening at the end of the straight cannula and into the eye.
Figure 16:
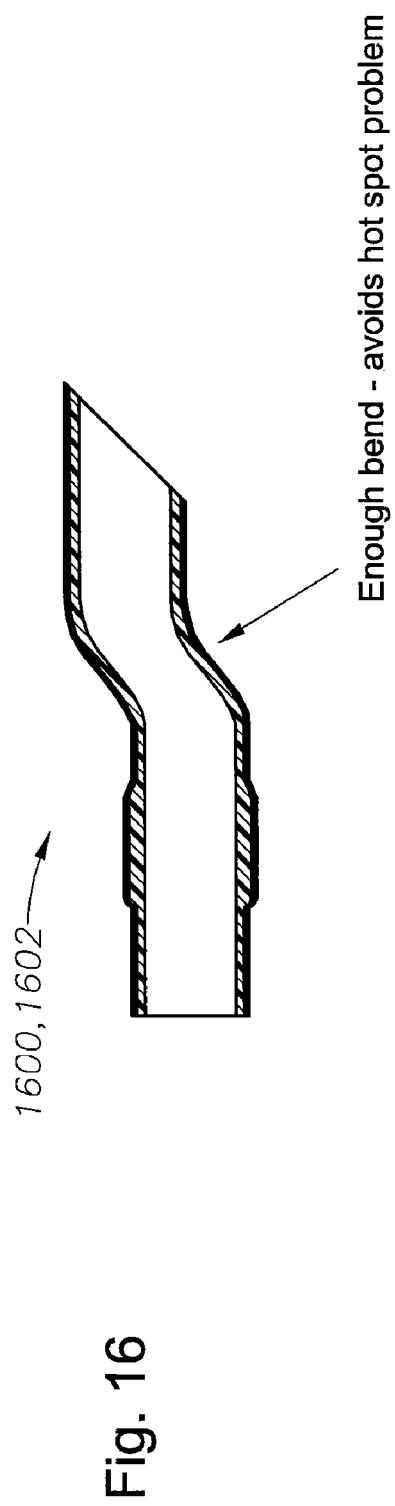
FIG. 16 depicts a solution to the "hot spot" problem illustrated in FIG. 15 in accordance with embodiments of the present invention.
Figure 17:
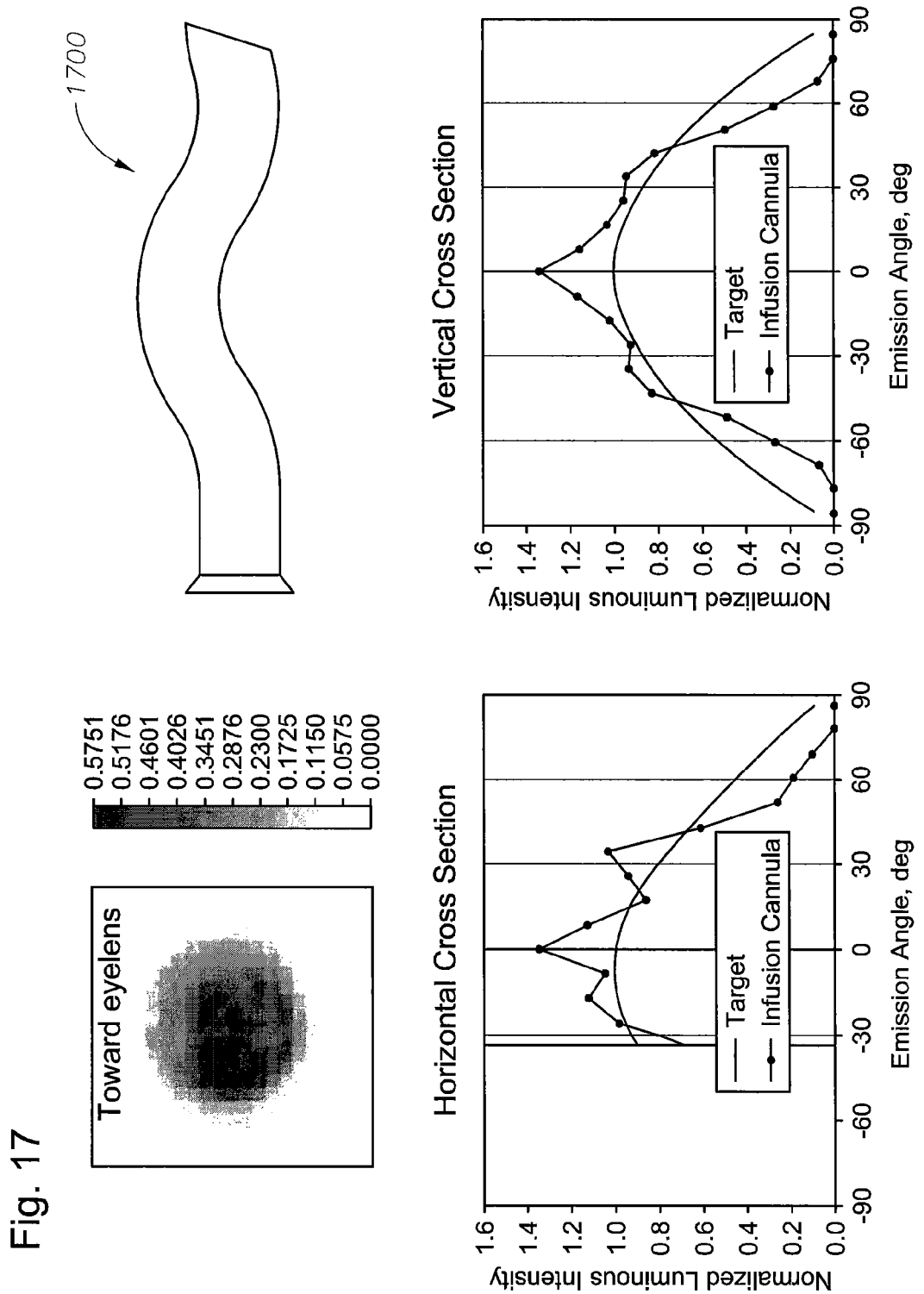
FIG. 17 depicts a solution to the "hot spot" problem illustrated in FIG. 15 that employs a curved metal cannula design that results in an angularly broad output beam in either gas (such as air) or liquid (such as saline solution) in accordance with embodiments of the present invention.

However, all of these features have a problem—a "hot spot" 1502 created by undiffused light 1504 passing directly from the distal end of the fiber 103/204 through the opening at the end of the straight cannula and into the eye (see FIG. 15). A solution to the hot spot problem is to curve the transparent cannula 1600 or opaque cannula 1602 in such a way that no rays of light can pass directly from the fiber 103/204 into the eye without hitting the cannula 1602 (see FIG. 16). Illustrated in FIG. 17 is a curved metal cannula design 1700 that results in an angularly broad output beam in either gas (such as air) or liquid (such as saline solution). Similar angular spread performance is achieved in the curved transparent cannula 1800 design of FIG. 18 (in which most of the cannula except the beveled distal end is coated with reflective metal.

Figure 19:
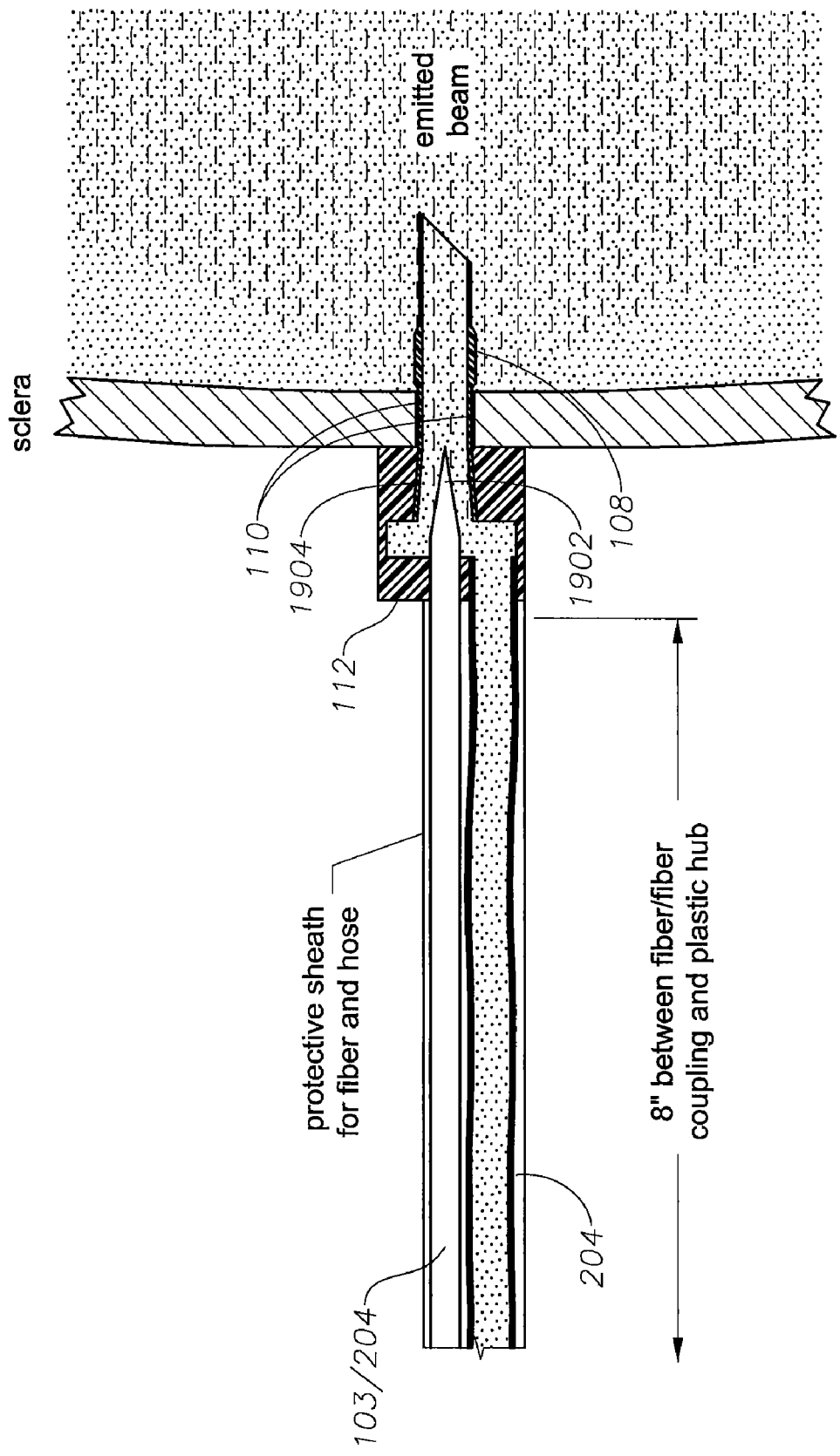
FIGS. 19-21 provide a representation of a transparent illuminated infusion cannula which incorporates a tapered fiber in accordance with embodiments of the present invention.
Figure 20:
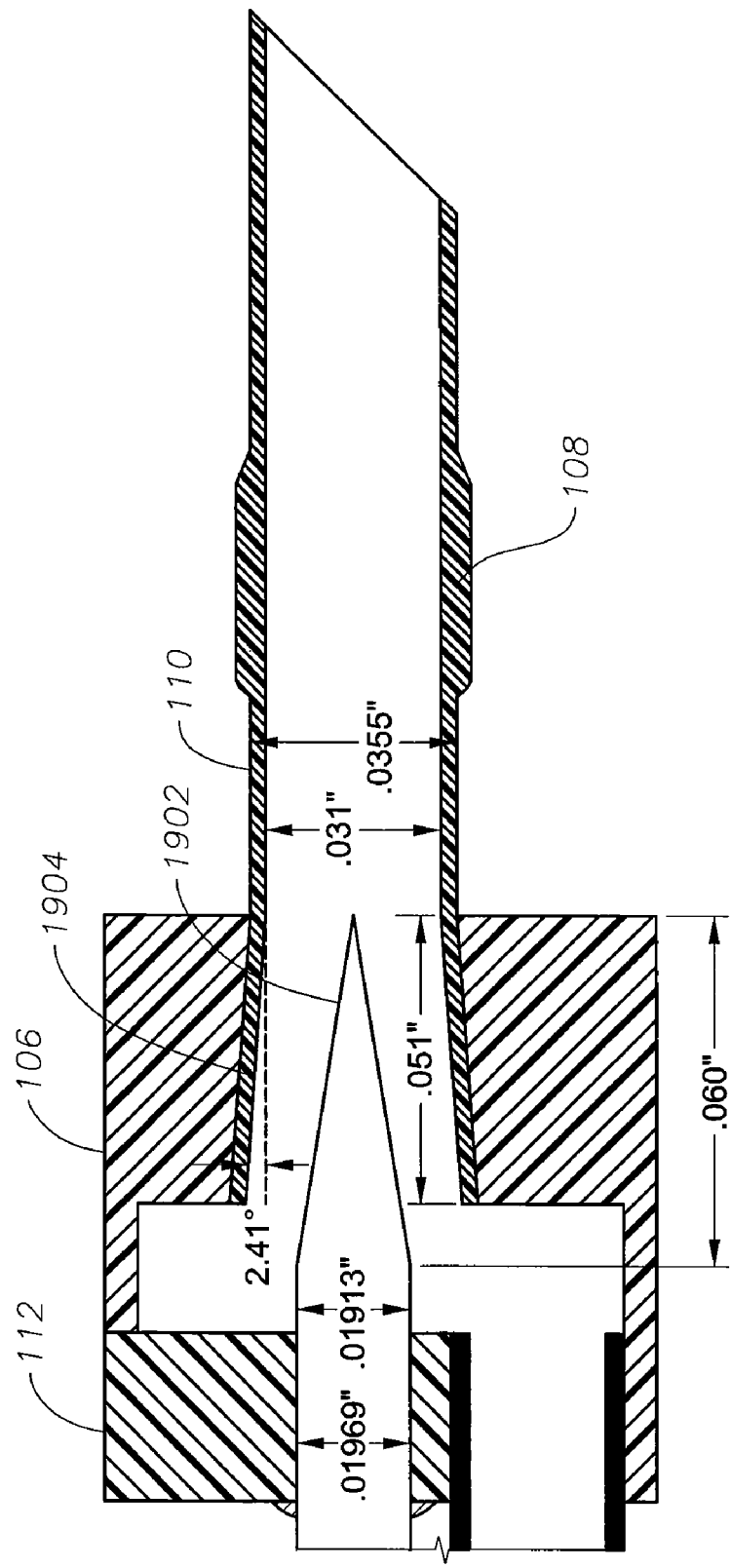
Figure 21:
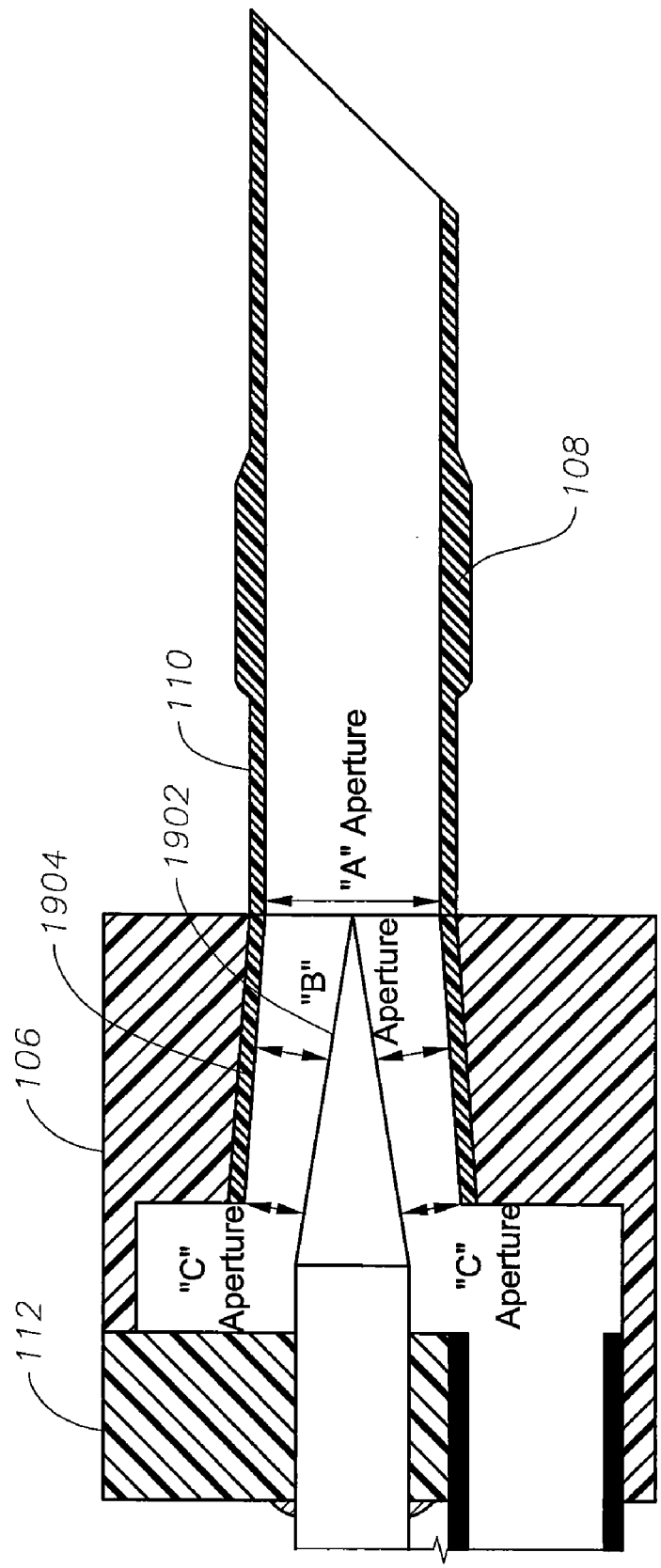
Figure 23:
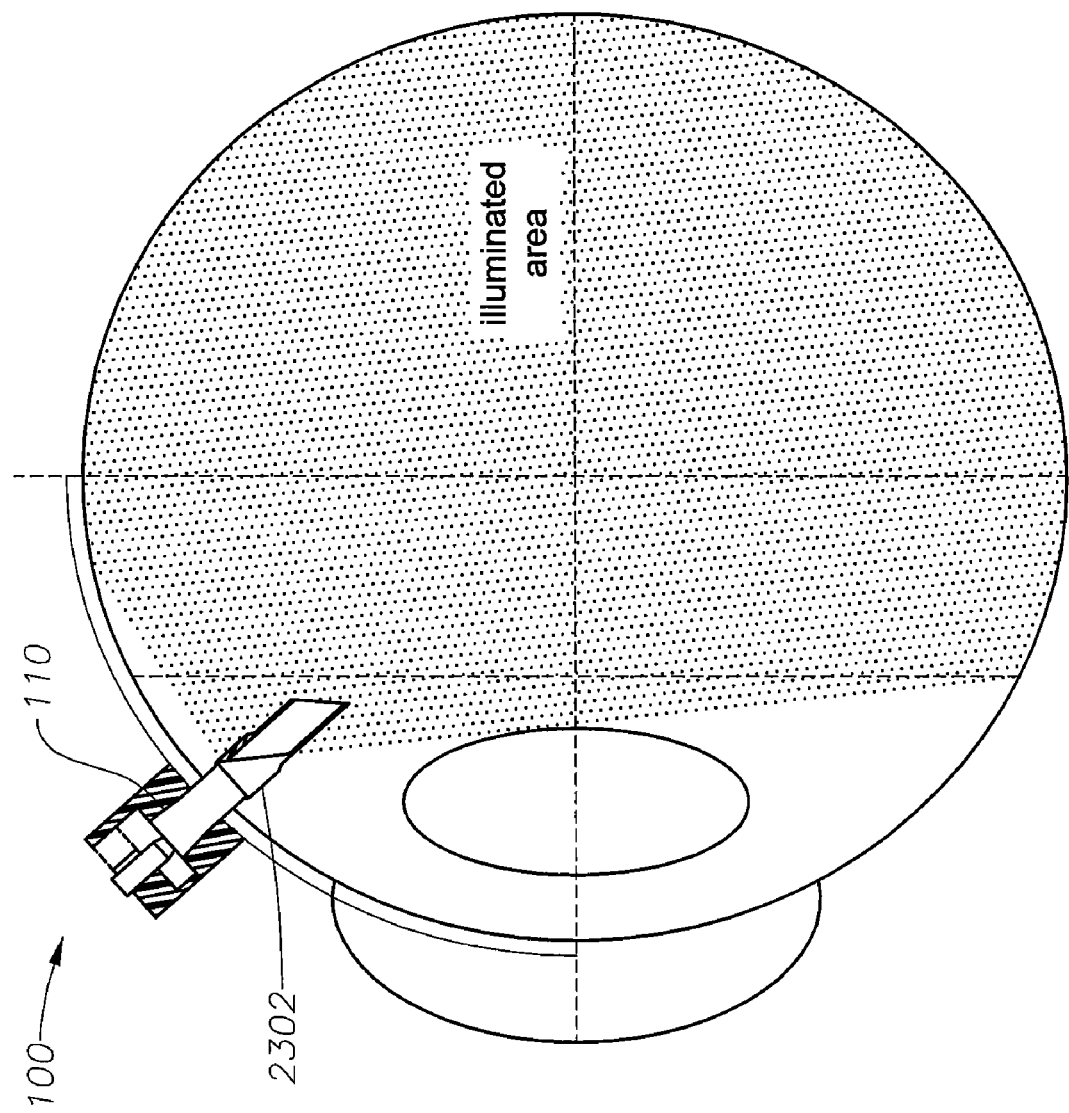
FIG. 23 provides a representation of a transparent illuminated infusion cannula having an angled reflective coating to prevent emitted light from directly illuminating the cannula in accordance with embodiments of the present invention.

The other means of angularly broadening the beam is to taper the distal end 1902 of the fiber 103/204. An embodiment of this invention, which incorporates a tapered fiber, is illustrated in FIGS. 19-21. In this preferred embodiment, proximal end 1904 of the cannula 108 is flared slightly so that the cross-sectional area between the fiber and cannula is no less than the area of the downstream end of the cannula (which is 0.000755 sq. in. in the example of FIGS. 20 and 21). The resultantly large angular spread of the emitted beam in air is illustrated in FIG. 22. This design has 36% greater light output and 71% greater cross-sectional flow area than the Synergetics approach. Additionally, an angled reflective coating 2302 can be added to the transparent cannula 100 as in FIG. 23 to prevent emitted light from directly illuminating the cannula.

Figure 24:
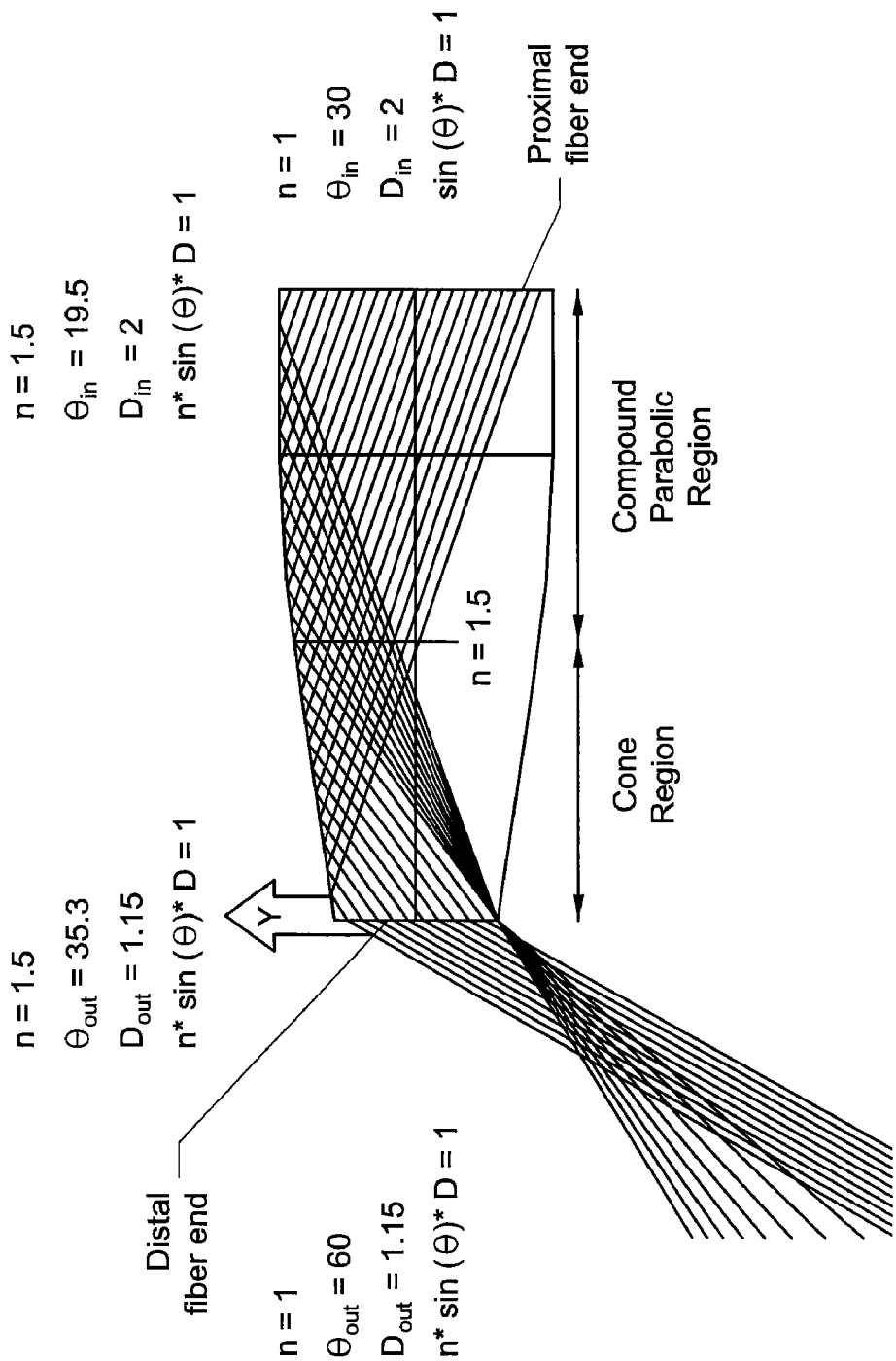
FIG. 24 provides a representation of fiber taper shape of a compound parabolic concentrator/truncated cone.

For a fiber which transports a beam with a beam half angle $\theta_{in}$, and which is designed to efficiently emit the light into an angularly uniform beam with half angle $\theta_{out}$, a linear taper is not the optimum taper shape. For a fictitious two-dimensional fiber (where the fiber and rays are entirely confined within a two-dimensional plane, the optimum taper shape would be a compound parabolic concentrator (CPC) butted up against a truncated linearly-tapered cone (as is illustrated in the example of FIG. 24). The ratio of the distal fiber diameter to proximal fiber diameter would equal to $\sin \theta_{in}/\sin \theta_{out}$. For this taper shape, neglecting Fresnel reflection losses, the efficiency of emission into the ambient air medium would be 100% and the resultant emitted beam would be uniform in luminance for angles as large as $\theta_{out}$ and would be zero for angles larger than $\theta_{out}$.

For a real three-dimensional fiber, the situation is more complicated. Some skew rays (skew rays are rays that pass outside of the plane that includes the fiber axis) which have off-axis angles less than $\theta_{in}$ will be turned around by total internal reflection and will pass back up the fiber towards the source. Likewise, some skew rays with off-axis angle greater than $\theta_{in}$ will pass out of the distal end of the tapered fiber. Therefore, for the real three-dimensional fiber the transmittance vs. angle profile of the emitted beam will not have an abrupt cutoff at $\theta_{out}$ but will roll off quickly, with the 50% transmittance point roughly at $\theta_{out}$. Furthermore, because of skew rays, the optimum-efficiency fiber taper shape is not the compound parabolic concentrator/truncated cone of FIG. 24 but a much more complex shape. The optimum shape is dependent in part on the exact luminance vs. angle characteristic of the beam coupled into the fiber, the fiber off-axis attenuation properties, and the exact desired output profile of the emitted beam. This optimum shape can be determined by using an optical design program such as Zemax that allows the fiber taper shape to be modified automatically until the optimum desired output is attained.

An embodiment of this invention is illustrated in FIGS. 19-21. In this embodiment, the fiber is linearly tapered and the efficiency of emission from the fiber is about 60%. This linear taper could be replaced by a complex taper shape similar to the CPC/truncated cone of FIG. 24, and the resultant fiber emission efficiency would be much closer to 100%. (The design of this optimum fiber taper shape would take into account the cannula reflectance and taper shape that would influence the output profile of the emitted beam) However, since for this optimum fiber taper shape the distal end of the fiber would not come to a point but instead would end in a small-diameter distal face, the cross-sectional flow area between this fiber and the cannula of FIGS. 19-21 would be restricted. In other words, the fluid would run into a bottleneck at the distal end of the fiber. This can be prevented by moving the optimum-taper fiber a small distance away from the cannula (towards the left in FIG. 20) and/or increasing the flare angle of the flared proximal end of the fiber. The resultant fiber/cannula combination would retain the high flow area of 0.000755 sq in and would potentially have even greater luminous throughput than the embodiment of FIGS. 19-21.

Therefore, an embodiment is that of FIGS. 19-21 that has been modified in the following way: the fiber taper shape, and cannula taper shape, and fiber/cannula relative positions are modified to yield a system that emits light uniformly across the entire retinal surface with optimum luminous flux efficiency.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention is described in detail, it should be understood that various changes, substitutions and alterations can be made hereto without departing from the spirit and scope of the invention as described.

What is claimed is:

1. An illuminated infusion cannula, comprising:
    an endo-illuminator operable to provide visible light at a distal end;
    a hose operable to transport a fluid;
    a hub mechanically coupled to the endo-illuminator and the hose; and
    a transparent cannula having a proximal end downstream from the hub and the distal end of the endo-illuminator, the transparent cannula allowing the visible light to be emitted through at least a portion of the transparent cannula wherein:
        the cannula is positioned coaxially with the endo-illuminator; and
        a space between the distal end of the endo-illuminator and the proximal end of the transparent cannula, wherein the space allows fluid to flow around the distal end of the endo-illuminator and into the transparent cannula.

2. The illuminated infusion cannula of claim 1, wherein a flow cross-sectional area is substantially constant within the hose, cannula, and interface between the hose, cannula and endo-illuminator.

3. The illuminated infusion cannula of claim 1, wherein the endo-illuminator comprises an optical fiber.

4. The illuminated infusion cannula of claim 3, wherein a distal end of the optical fiber is shaped and wherein the optical fiber/transparent cannula emit light substantially uniformly.

5. The illuminated infusion cannula of claim 1, wherein the distal end of the endo-illuminator is tapered and the proximal end of the transparent cannula is flared.

6. The illuminated infusion cannula of claim 1, wherein at least a portion of the cannula reflects light emitted from the endo-illuminator.

7. The illuminated infusion cannula of claim 1, wherein the cannula disperses light emitted from the endo-illuminator in a desired angular distribution.

8. The illuminated infusion cannula of claim 1, wherein a diffusive surface, a diffractive surface, and/or a micro lens array is operable to disperse light emitted from the endo-illuminator in a desired angular distribution.

9. The illuminated infusion cannula of claim 7, wherein the cannula is curved such that no light emitted from the endo-illuminator is directly transmitted from the cannula.

10. A transparent illuminated infusion cannula, comprising:
    an endo-illuminator operable to provide visible light at a distal end to illuminate an area within an eye;
    a hose operable to transport a fluid;
    a protective sheath operable to combine the endo-illuminator and hose within a single cable;
    an incision cannula operable to incise the sclera of the eye; and
    a transparent cannula within the incision cannula having a proximal end downstream of the distal end of the endo-illuminator, the transparent cannula allowing the visible light to be emitted through at least a portion of the transparent cannula wherein:
        the transparent cannula is positioned coaxially with the endo-illuminator; and
        a space between the distal end of the endo-illuminator and the proximal end of the transparent cannula allows fluid to flow around the distal end of the endo-illuminator, into the transparent cannula, and into a sclera aperture.

11. The illuminated infusion cannula of claim 10, wherein a flow cross-sectional area is substantially constant within the hose, cannula, and interface between the hose, cannula and endo-illuminator.

12. The illuminated infusion cannula of claim 10, wherein the endo-illuminator comprises an optical fiber.

13. The illuminated infusion cannula of claim 12, wherein a distal end of the optical fiber is shaped and wherein the optical fiber/transparent cannula emit light substantially uniformly.

14. The illuminated infusion cannula of claim 10, wherein the distal end of the endo-illuminator is tapered and the proximal end of the transparent cannula is flared.

15. The illuminated infusion cannula of claim 10, wherein at least a portion of the cannula reflects light emitted from the endo-illuminator.

16. The illuminated infusion cannula of claim 10, wherein the cannula disperses light emitted from the endo-illuminator in a desired angular distribution.

17. The illuminated infusion cannula of claim 11, wherein a diffusive surface, a diffractive surface, and/or a micro lens array is operable to disperse light emitted from the endo-illuminator in a desired angular distribution.

18. The illuminated infusion cannula of claim 16, wherein the cannula is curved such that no light emitted from the endo-illuminator is directly transmitted from the cannula.

19. A transparent illuminated infusion cannula, comprising:
    an optical fiber operable to provide visible light at a distal end to illuminate an area within an eye;
    a hose operable to transport a fluid;
    a protective sheath operable to combine the optical fiber and hose within a single cable;
    an incision cannula operable to incise the sclera of the eye; and
    a transparent cannula within the incision cannula having a proximal end downstream of the distal end of the optical fiber, the transparent cannula allowing the visible light to be emitted through at least a portion of the transparent cannula wherein:
        the transparent cannula is positioned coaxially with the optical fiber; and
        a space between the distal end of the optical fiber and the proximal end of the transparent cannula allows fluid to flow around the distal end of the optical fiber, into the transparent cannula, and into a sclera aperture, and wherein a flow cross-sectional area is substantially constant within the hose, cannula, and interface between the hose, cannula and optical fiber.

20. The illuminated infusion cannula of claim 19, wherein a distal end of the optical fiber is shaped and wherein the optical fiber/transparent cannula emit light substantially uniformly.

21. The illuminated infusion cannula of claim 19, wherein the distal end of the optical fiber is tapered and the proximal end of the transparent cannula is flared.

22. The illuminated infusion cannula of claim 19, wherein the transparent cannula comprises an annular bump operable at to anchor the transparent cannula to the eye after insertion.

23. The illuminated infusion cannula of claim 19, wherein the cannula disperses light emitted from the optical fiber in a desired angular distribution.

24. The illuminated infusion cannula of claim 23, wherein a diffusive surface, a diffractive surface, and/or a micro lens array is operable to disperse light emitted from the optical fiber in a desired angular distribution.

* * * * *